United States Patent [19]

Scott

[11] Patent Number: 4,878,490
[45] Date of Patent: Nov. 7, 1989

[54] UNIVERSAL ORTHOPEDIC RECUPERATIVE GARMENT

[76] Inventor: James W. Scott, P.O. Box 7630, Tifton, Ga. 31794

[21] Appl. No.: 302,364

[22] Filed: Jan. 27, 1989

[51] Int. Cl.$^4$ ............................................. A61F 5/37
[52] U.S. Cl. ...................................... 128/77; 128/78; 128/165
[58] Field of Search ..................... 128/77, 165, 78, 94, 128/133, 134; 2/16, 44, 45, 107, 309, 310, 311, 313

[56] References Cited

U.S. PATENT DOCUMENTS

| | | |
|---|---|---|
| 980,464 | 1/1911 | Wermuth . |
| 1,266,688 | 5/1918 | Kassner . |
| 1,596,297 | 8/1926 | Oelgoetz ............................... 128/78 |
| 1,621,323 | 3/1927 | Horn . |
| 2,344,844 | 3/1944 | Baldeschwieler . |
| 2,512,474 | 6/1950 | Baldeschwieler . |
| 3,559,640 | 2/1971 | Beckett . |
| 4,171,542 | 10/1979 | Cox et al. . |
| 4,550,724 | 11/1985 | Berrehail ............................. 128/165 |
| 4,601,285 | 7/1986 | Whitchurch . |
| 4,628,913 | 12/1986 | Lerman ................................. 128/68 |
| 4,644,939 | 2/1987 | Coleman .............................. 128/78 |
| 4,733,658 | 3/1988 | Ruthven, Jr. . |
| 4,759,353 | 7/1988 | Melendez et al. ..................... 128/77 |

FOREIGN PATENT DOCUMENTS 2181952  5/1987  United Kingdom ................. 128/77

Primary Examiner—Edgar S. Burr
Assistant Examiner—Huong Q. Pham
Attorney, Agent, or Firm—Bradford E. Kile

[57] ABSTRACT

A universal orthopedic recuperative garment to be worn following corrective surgery or substantial trauma to an arm and/or shoulder including a vest portion to be fitted over the head of a patient, a means to secure the vest around a patient's lower torso, an arm support panel which attaches to the vest portion to fashion a generally horizontal channel and cradle a patient's forearm, and an upper arm rotating and binding strap which attaches to a front portion of the vest to provide a desired degree of left and rotation of a patient's shoulder.

14 Claims, 2 Drawing Sheets

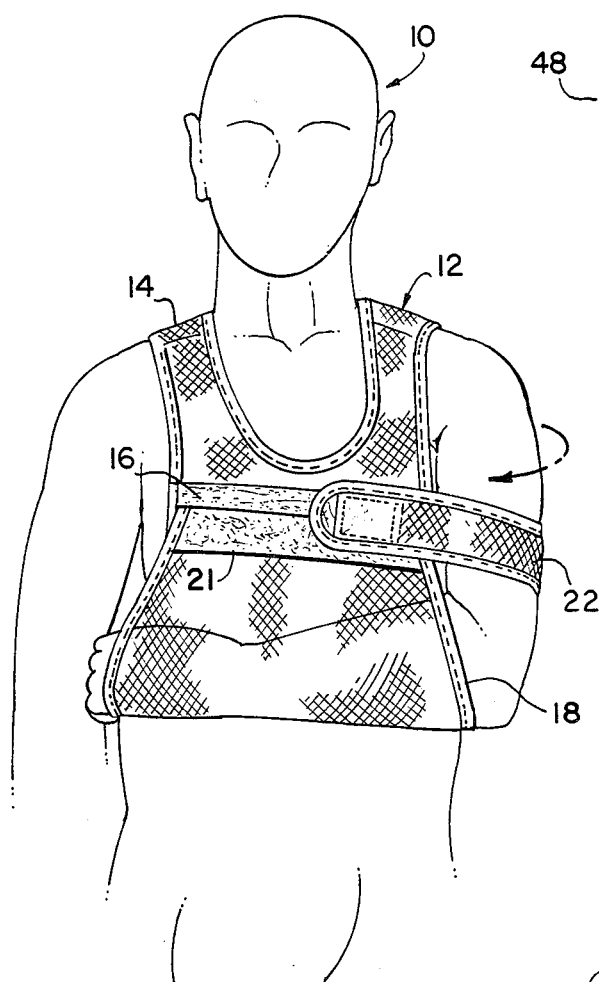
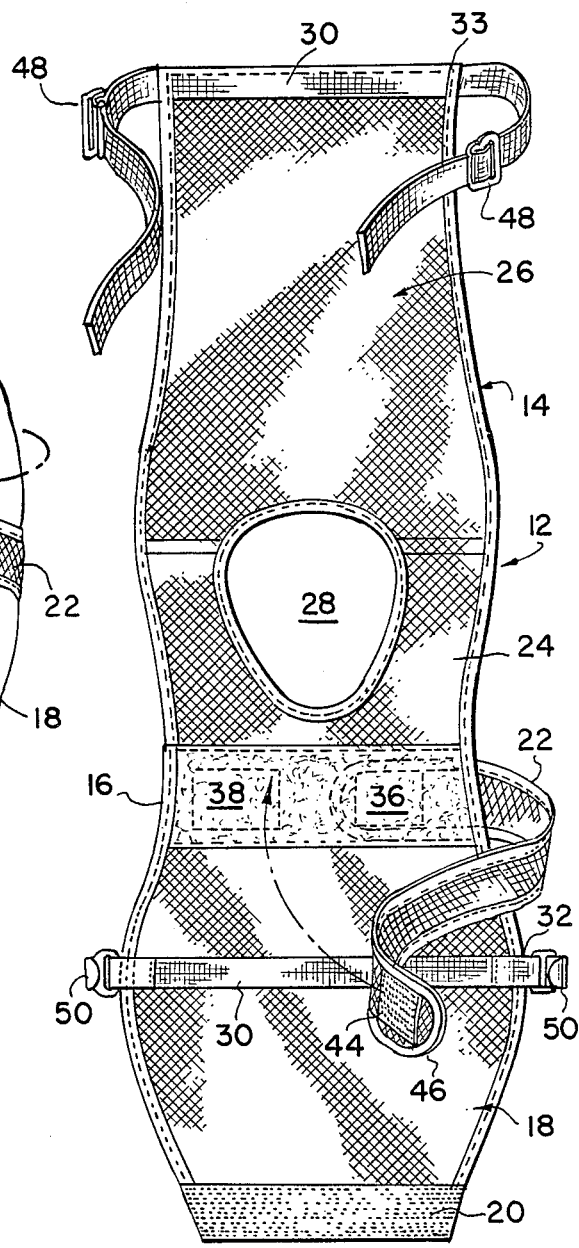
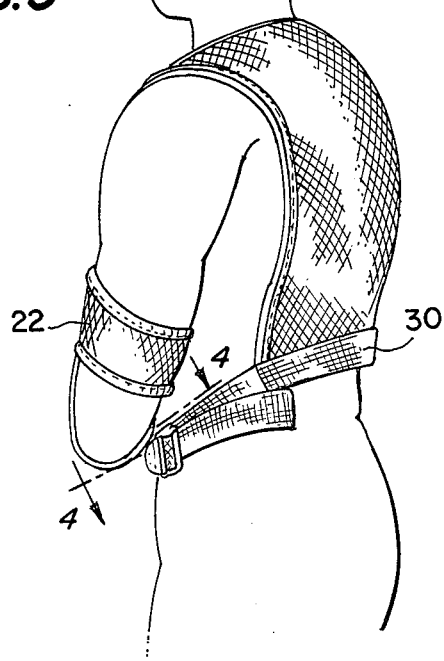
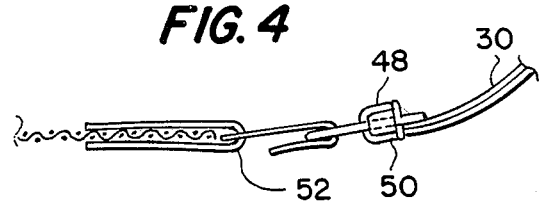

UNIVERSAL ORTHOPEDIC RECUPERATIVE GARMENT

BACKGROUND OF THE INVENTION

This invention relates to a universal orthopedic recuperative garment. More particularly, this invention relates to a universal orthopedic recuperative garment to be worn following corrective surgery or substantial trauma to a patient's shoulder, arm, wrist, or hand requiring temporary, recuperative immobilization.

Following reconstructive surgery on a shoulder, scapular arch, arm, wrist, or hand such as repairing a chronic dislocating shoulder, mild subluxations, tears and avulsions of the glenoid labrum, and tears of the rotator cuff, as well as after certain types of fractures of the arm and/or shoulder, it is necessary to place and support a damaged member in a relatively immobile posture during recuperation.

In the past, physicians have utilized expedient constructs such, as for example, slings made from a simple circular strap extending around a patient's neck and wrist. Such devices tended, however, to exert undue localized pressure upon a patient's neck and to a lesser degree the patient's wrist.

Localized pressure difficulties were alleviated, somewhat with the use of folded and shaped cloth slings. These improved load distributing devices, however, do not provide an opportunity to provide correct placement of a patient's arm following many operative procedures.

In addition to the above, numerous specialty slings have been envisioned. In each instance, however, they have exhibited one or more limitations such as being too specialized for a particular injury to be of general utility.

In addition to obviating limitations of the type described above it would be desirable to be able to support a patient's arm in a horizontal position across a patient's chest in a raised and rotated posture from the patient's shoulder.

The difficulties and limitations noted in the proceeding are not intended to be exhaustive but rather are among many which may tend to reduce the effectiveness and physician/patient satisfaction with prior arm support devices. Other noteworthy problems may exist; however, those presented above should be sufficient to demonstrate that arm support devices appearing in the past will admit to worthwhile improvement.

OBJECTS and BRIEF SUMMARY OF THE INVENTION

Objects

It is therefore a general object of the invention to provide a novel universal orthopedic recuperative garment which will obviate or minimize difficulties of the type previously described.

It is a specific object of the invention to provide a universal orthopedic recuperative garment which will provide a relatively comfortable arm support that minimizes pressure on a patient's neck.

It is still another object of the invention to provide a universal orthopedic recuperative garment which may be used with or without a cast on a patient's arm.

It is a further object of the invention to provide a universal orthopedic recuperative garment which may be facilely adjustable to accommodate a range of arm heights.

It is yet a further object of the invention to provide a universal orthopedic recuperative garment which will insure horizontal immobilization of a patient's arm.

It is another object of the invention to provide a universal orthopedic recuperative garment which is universal and easily adjustable by doctor and/or patient to redressing of wounds, removal of stitches, application of local treatment, etc. as well as intervention for personal hygiene when the subject invention is not used in cooperation with a plaster cast.

It is still a further object of the invention to provide a universal orthopedic recuperative garment operable to rotate a patient's shoulder by lifting the humerus portion of a patient's arm and/or further rotate the patient's shoulder by pulling a patient's humerus toward a central longitudinal axis of a patient's body.

It is additionally an object of the invention to provide a universal orthopedic recuperative garment which will not bind a patient's elbow whereby result in minor pain and/or more intolerable ankylosis.

Brief Summary of a Preferred Embodiment of the Invention

A preferred embodiment of the invention which is intended to accomplish at least some of the foregoing objects includes a vest portion having a front vest panel and a back vest panel. The front vest panel is substantially coextensive with the back panel and includes an opening which can be fitted over the head of a patient such that the vest is worn on a patient's shoulders. The front vest panel also includes a generally rectangular retaining pad which laterally extends across an upper portion of the front panel and at least one retaining patch mounted upon an interior surface of the front panel and directly opposed to the rectangular retaining pad. The front and back vest panels are joined at a patient's lateral rib cage areas by adjustable means connected to the lateral edges of the vest panels.

An arm support panel having a pair of first and second transverse rectangular strips mounted on both faces of a free end of the arm panel integrally joins a bottom portion of the front vest panel. The first transverse rectangular strip releasably connects to the rectangular retaining pad allowing the arm support panel to fold upward and form in cooperation with the front vest panel a transversely extending channel to cradle a patient's forearm. The second opposed transverse rectangular strip horizontally spans the rectangular retaining pad to form an outwardly extending retaining surface.

An upper arm rotating and binding strap has a fastening patch mounted on either end whereby the rotating and binding strap releasably attaches to the retaining patch located on the interior surface of the front vest panel. The rotating and binding strap wraps around a patient's upper arm and finally attaches to an outwardly extending retaining surface at the other end. Utilization of this strap enables a physician to selectively pull a patient's humerus forward and rotate the humerus while the patient's forearm is supported by the transversely extending channel formed by the front vest panel and the arm support panel.

THE DRAWINGS

Other objects and advantages of the present invention will become apparent from the following detailed description of a preferred embodiment thereof taken in conjunction with the accompanying drawings, wherein:

FIG. 1 is a view disclosing the context of the subject invention and depicts a patient wearing a vest which includes an arm sling portion and an upper arm rotating and binding strap to securely bind and rotate a patient's left recuperative arm in accordance with a preferred embodiment of the invention;

FIG. 2 is a plan view of a preferred embodiment of the subject universal orthopedic recuperative garment 10 in a flat condition;

FIG. 3 is a side detail view of the subject invention showing the upper arm rotating and binding strap applied to shift the arm forward with respect to a patient's side and an adjustable strap which encircles the patient's lower torso;

FIG. 4 is a detailed segmental view of the adjustable strap, as viewed in the direction of sight line 4—4 in FIG. 3;

Figure 5:
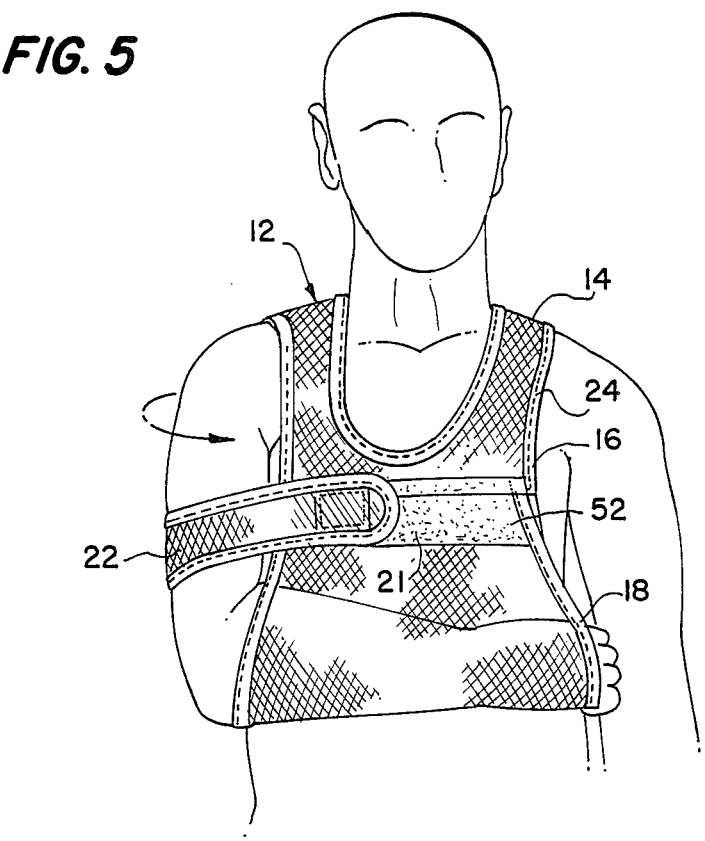
Figure 6:
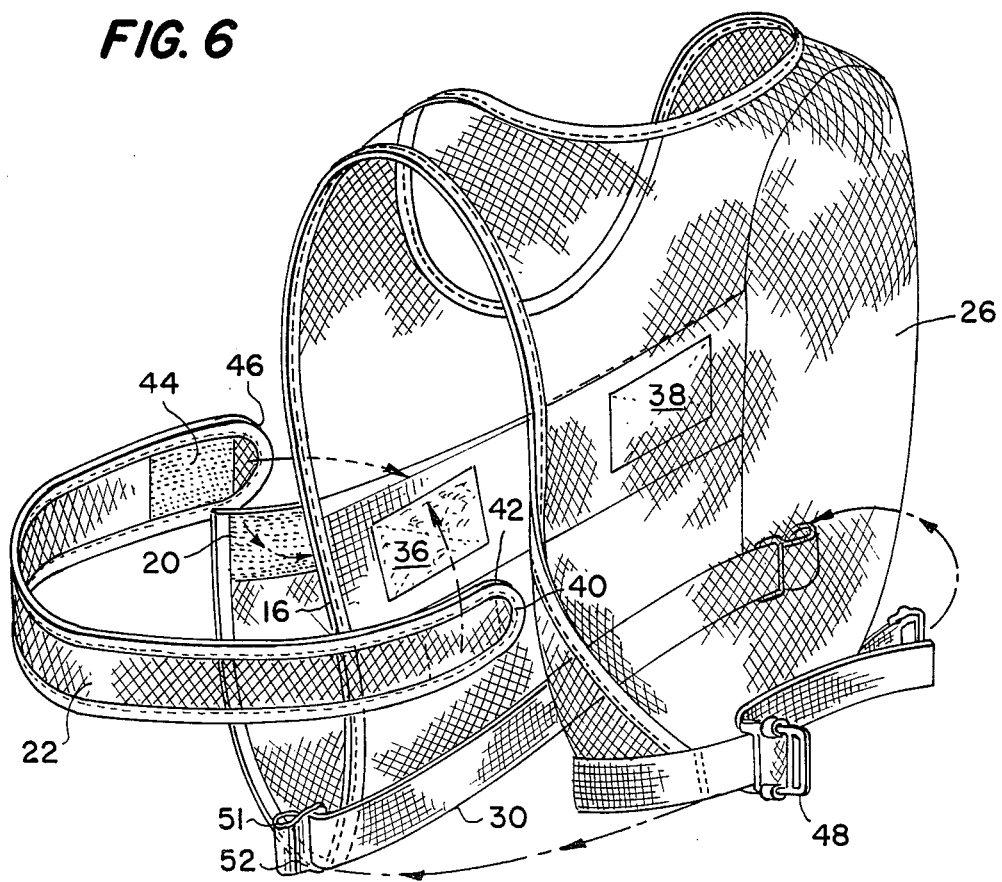

FIG. 5 is a detailed front view of the subject universal orthopedic recuperative garment in an alternative preferred mode to bind and rotate a patient's right recuperative arm; and FIG. 6 is an exploded assembly view of the subject universal orthopedic recuperative garment which includes a front vest panel, a back vest panel, a generally rectangular retaining pad, an adjustable strap, an arm support panel, and an upper arm rotating and binding strap.

DETAILED DESCRIPTION

Referring now to the drawings, wherein like numerals indicate like parts, and initially to FIG. 1, there will be seen an operative context of the subject invention. More particularly, a patient 10 is shown wearing a universal orthopedic recuperative garment 12 in accordance with a preferred embodiment of the invention. The subject universal orthopedic recuperative garment 12 includes a vest portion 14, a generally rectangular retaining pad 16, an arm support panel 18 having a pair of transverse rectangular strip 20 (note FIG. 6) and 21, and an upper arm rotating and binding strap 22.

Turning now specifically to FIG. 2 there will be seen a plan view of the external surface of the subject universal orthopedic recuperative garment 12. The vest portion 14 includes a front vest panel 24 operable to extend over a patient's chest and upper torso and a back vest panel 26 joined to and substantially coextensive with the front vest panel 24. The front and back vest panels 24 and 26 are joined and a central opening 28 if formed to permit the universal orthopedic recuperative vest 14 to be fitted over the head of a patient. Accordingly the weight of the vest 14 and the weight of a patient's arm may be evenly distributed across a patient's shoulders.

An adjustable strap 30 directly attaches to bottom portions 32 and 33 of the front and back vest panels 24 and 26 respectively of said vest portion 14 for securing said vest portion 14 about a patient's upper torso by shortening or elongating said adjustable strap 30.

The front panel 24 serves as a base for the generally rectangular retaining pad 16; which is composed of a pile type fastening material and laterally extends across an upper portion of the front vest panel 24. The arm support panel 18 integrally joins the bottom portion 32 of the front vest panel 24 and has a pair of transverse rectangular strips 20 and 21 mounted on either side of a free end 34 of the arm support panel 18. A first transverse rectangular strip 20 is mounted on one side of the free end 34 of said arm support panel 18 and a second opposed transverse rectangular strip 21 is mounted on an opposed side of the free end 34 of said arm support panel 18. The arm support panel 18 and the front and back panels 24 and 26 of the vest are preferably composed of an open mesh nylon material or the like.

Still referring to FIG. 2, and in addition FIG. 6, a pair of retaining patches 36 and 38 composed of a pile type fastening material are mounted upon an interior surface of said front vest panel 24. Patches 36 and 38 are opposed or positioned behind said generally rectangular retaining pad 16. An upper arm rotating and binding strap 22 shown attached to the front vest panel 24 at one retaining patch 36, has a first fastening patch 40 at a first end 42, shown with phantom lines in FIG. 2, and a second fastening patch 44 at a second free end 46. The pair of fastening patches 40 and 44 are composed of a hook type fastening material.

Referring particularly to FIG. 3, the upper arm rotating and binding strap 22 pulls a patient's upper arm forward with respect to a patient's side to rotate a patient's shoulder. Also the adjustable strap 30 encircles a lower torso area of a patient when connected at a patient's lateral rib cage areas to form a continuous band around a patient's lower torso.

The adjustable strap 30, as seen in a sectional view in FIG. 4, comprises an adjustable clasp 48 and a hoop connector 50 which interlock to join the front and back vest panels 24 and 26. The adjustable strap 30 may be elongated or shortened through the adjustable clasp 48 to conform to the waist size of a patient.

Turning now at FIG. 5, an alternative operating condition is presented in contrast to FIG. 1 wherein the universal orthopedic recuperative garment 12 is shown supporting a patient's right arm. Here the upper arm rotating and binding strap 22 is releasably attached at one end to a retaining pad 38, noted FIG. 6, mounted on the right interior surface of the front vest panel 24 and at the other end to an outwardly extending retaining surface 52 formed from a combination of the rectangular retaining pad 16 and the second opposed transverse rectangular strip 21 Accordingly, the upper arm rotating and binding strap 22 extends from an interior portion of the front vest panel 24, around a humerus portion of a patient's right arm and connects to the outwardly extending retaining surface 52.

The attachments of the various hook and pile type fastening strips are shown in FIG. 6. The first transverse strip 20 is composed of a hook type fastening material and releasably connects to the generally rectangular retaining pad 16. This attachment allows the arm support panel 18 to fold upward and transversely attach to the generally rectangular retaining pad 16 mounted upon the front vest panel 24. Accordingly, a transversely extending channel 21 is formed by the front vest panel 24 and the arm support panel 18, with a degree of vertical adjustment, for supporting a patient's forearm. This connection also forms the outwardly extending retaining surface 52 as discussed above in association with FIG. 5. The upper arm rotating and binding strap 22 is connected to an interior portion of the front vest panel 24 by operably combining the hook type material fastening patch 40 to the pile type material retaining patch 36 located on the interior surface of said front vest panel 24. After being wrapped around the upper humerus portion of a patient's arm, the hook type material fastening patch 44 of the rotating and binding strap 22 is connected to the outward retaining surface 52. The vertical and horizontal expanse of surface 52 permits a physician to lift and rotate a patient's recuperative arm with a range of elevation and rotation.

SUMMARY OF THE MAJOR ADVANTAGES OF THE INVENTION

After reading and understanding the foregoing inventive universal orthopedic recuperative garment, description of the subject in conjunction with the drawings, it will be appreciated that several distinct advantages of the subject invention are obtained.

Without attempting to set forth all the desirable features of the instant universal orthopedic recuperative garment, at least some of the major advantages of the invention include the combination of a front vest panel 24 integrally joined to a back vest panel 26 which form a vest portion 14 having a central opening 28 operable to permit the vest portion 14 to be fitted over the head of a patient. This arrangement evenly distributes supporting loads over the shoulders of a patient as opposed to a conventional arm support arrangement which places localized pressure on a patient's neck.

The arm support panel 18 in conjunction with the front vest panel 24, creates a transversely extending channel 51 which will insure horizontal immobilization of a patient's arm. Still further, the subject universal orthopedic recuperative garment 12 may be used with or without a cast. The transversely extending channel, formed by panel 18; however, frequently provides adequate stability for a recuperating arm without the additional need for a plaster cast. At the same time, if a cast is used, the panel provides space to accommodate the extra width of an arm immobilized in a cast.

The arm support panel 18 may be folded upwardly to any desired height since the first transverse rectangular strip 20 may releasably attach to the rectangular retaining pad 16 at various vertical levels. This allows a physician to adjust the height of the recuperating arm during the recuperative stage of healing.

The upper arm binding and rotating strap 22, having fastening patches 40 and 42, can be releasably attached to the front vest panel 24 about the left or right arm to provide a universal aspect of the subject invention. Further, the hook and pile type fastening patches 40 and 44 allow a doctor to easily manipulate or adjust the degree of rotation of a patient's shoulder and/or arm during recuperation. In a similar vein, the releasable patches 40 and 44 allow a patient to remove the subject invention to change dressings or clean the recuperative member.

Further, the upper arm binding and rotating strap 22 is attached at one end to one of a pair of retaining patches 36 and 38 mounted on the interior surface of the front vest panel 24 and then may be attached at the other end anywhere on the outwardly extending retaining surface 52, formed by members 16 and 21, allowing a physician to rotate a patient's shoulder at various degrees by lifting the humerus portion of a patient's arm forward with respect to a patient's side.

Still further, he upper arm 22 strap does not bind a patient's elbow. Binding the elbow of a patient often results in discomfort or in some cases severe ankylosis.

In describing the invention, reference has been made to a preferred embodiment and illustrative advantages of the invention. Those skilled in the art, however, and familiar with the instant disclosure of the subject invention, may recognize additions, deletions, modifications, substitutions and other changes which will fall within the purview of the subject invention and claims.

What is claimed is:

1. A universal orthopedic recuperative garment comprising:
   a vest portion having,
      a front vest panel operable to extend over a patient's chest and upper abdomen, and
      a back vest panel joined to and substantially coextensive with said front vest panel, said front and back vest panels having a central opening operable to permit said vest to be fitted over the head of a patient such that said vest may be operably supported upon a patient's shoulders;
   a generally rectangular retaining pad laterally extending across an upper portion of said front panel and being composed of one of a hook and pile type fastening material;
   means connected to adjacent lateral edges of said front panel and said back panel for adjustably connecting said front and back panels substantially at lateral rib cage areas for securing said vest portion about the upper torso of a patient;
   an arm support panel integrally joined at a bottom portion of said front vest panel, said arm support panel, having at a free end thereof, a transverse rectangular strip on each side of said free end is composed of one of a hook and pile type fastening material wherein a first transverse rectangular strip releasably connects to said generally rectangular retaining pad and a second opposed transverse rectangular strip forms an outwardly extending retaining surface in cooperation with said generally rectangular retaining pad composed of one of a hook and pile type fastening material thereby allowing said arm support panel to fold upwardly and transversely attach to said generally rectangular retaining pad mounted upon said front vest panel and to form from said front vest panel and said arm support panel a transversely extending channel for supporting a patient's forearm;
   at least one retaining patch mounted upon an interior surface of said front panel and opposed to said generally rectangular retaining pad and being composed of one of a hook and pile type fastening material; and
   an upper arm rotating and binding strap having fastening patch at a first end composed of the other of a hook and pile type fastening material with respect to said one of said hook and pile type fastening material of said outwardly extending retaining surface of said generally rectangular retaining pad and said transverse rectangular strip and a fastening patch at a second end of said upper arm rotating and binding strip composed of the other of a hook and pile type fastening material with respect to said at least one retaining patch positioned on the interior surface of said front vest panel wherein a patient's recuperating hand, forearm, upper arm, shoulder, or the like may be operably supported by placing a patient's forearm in a generally horizontal posture within said transversely extending channel formed by said front vest panel and said arm support panel and the patient's upper arm is pulled forward and rotated by said arm rotating and binding strap extending from an interior portion of said front vest panel, around the upper humerus portion of patient's arm and connecting to said outwardly extending retaining surface formed upon said front vest panel of said universal orthopedic recuperative garment.

2. A universal orthopedic recuperative garment as defined in claim 1 wherein said at least one retaining patch comprises:
 a first retaining patch mounted upon an interior surface of said front vest panel adjacent a first edge of said front vest panel and being composed of one of a hook and pile type fastening material; and
 a second retaining patch mounted upon an interior surface of said front vest panel adjacent a second edge of said front vest panel and being composed of the same of a hook and pile type fastening material with respect to said first retaining patch.

3. A universal orthopedic recuperative garment as defined in claim 1 wherein:
 said front vest panel and said back vest panel are composed of an open mesh material.

4. A universal orthopedic recuperative garment as defined in claim 3 wherein:
 said arm support panel is composed of an open mesh material.

5. A universal orthopedic recuperative garment as defined in claim 3 wherein:
 said upper arm rotating and binding strap is composed of an open mesh material.

6. A universal orthopedic recuperative garment as defined in claim 3 wherein said means connected to adjacent lateral edges of said front and back panels comprises:
 an adjustable strap for adjustably connecting said front and back panels substantially at lateral rib cage areas of a patient for securing said vest portion about the upper torso of a patient by shortening or elongating said adjustable strap.

7. A universal orthopedic recuperative garment as defined in claim 6 wherein:
 said adjustable strap encircles the lower torso of a patient when connected at the lateral rib cage areas forming a continuous band around the patient's lower torso being securely fastened to a bottom edge of said front and back panels and adjustable at the lateral rib cage areas.

8. A universal orthopedic recuperative garment as defined in claim 1 wherein:
 said outwardly extending retaining surface of said generally rectangular retaining pad mounted on said front vest panel and said second opposed transverse rectangular strip mounted on said free end of said arm support panel is composed of a pile type fastening material.

9. A universal orthopedic recuperative garment as defined in claim 8 wherein:
 said first transverse rectangular strip mounted on said free end of said arm support panel is composed of a hook type fastening material to releasably connect to said generally rectangular retaining pad.

10. A universal orthopedic recuperative garment as defined in claim 9 wherein:
 said first and second fastening patches mounted on said arm rotating and binding strap are composed of hook type fastening material.

11. A universal orthopedic recuperative garment comprising:
 a vest portion being composed of an open mesh material having,
  a front vest panel operable to extend over a patient's chest and upper abdomen, and
  a back vest panel joined to and substantially coextensive with said front vest panel, said front and back vest panels having a central opening operable to permit said vest to be fitted over the head of a patient such that said vest may be operably supported upon a patient's shoulders;
 a generally rectangular retaining pad laterally extending across an upper portion of said front panel and being composed of one of a pile type fastening material;
 means connected to adjacent lateral edges of said front panel and said back panel for adjustably connecting said front and back panels substantially at lateral rib cage areas for securing said vest portion about the upper torso of a patient;
 an arm support panel composed of an open mesh material and integrally joined at a bottom portion of said front vest panel, said arm support panel, having at a free end thereof, a transverse rectangular strip on each side of said free end composed of one of a hook and pile type fastening material wherein a first transverse rectangular strip releasably connects to said generally rectangular retaining pad and a second opposed transverse rectangular strip forms an outwardly extending retaining surface in cooperation with said generally rectangular retaining pad composed of a pile type fastening material thereby allowing said arm support panel to fold upwardly and transversely attach to said generally rectangular retaining pad mounted upon said front vest panel and to form from said front vest panel and said arm support panel a transversely extending channel for supporting a patient's forearm;
 a first retaining patch mounted upon an interior surface of said front panel adjacent a first edge of said front vest panel and being composed of one of a hook and pile type fastening material;
 a second retaining patch mounted upon an interior surface of said front vest panel and adjacent a second edge of said front vest panel and being composed of one of a hook and pile type fastening material which is the same as said first retaining patch; and
 an upper arm rotating and binding strap composed of an open mesh material having a fastening patch at a first end composed of the other of a hook and pile type fastening material with respect to said one of said hook and pile type fastening material of said outwardly extending retaining surface of said generally rectangular retaining pad and said transverse rectangular strip and a fastening patch at a second end of said upper arm rotating and binding strap composed of the other of a hook and pile type fastening material with respect to said at least one retaining patch positioned on the interior surface of said front vest panel wherein a patient's recuperating hand, forearm, upper arm, shoulder, or the like may be operably supported by placing a patient's forearm in a generally horizontal posture within said transversely extending channel formed by said front vest panel and said arm support panel and the patient's upper arm is pulled forward and rotated by said arm rotating and binding strap extending from an interior portion of said front vest panel, around the upper humerus portion of patient's arm and connecting to said outwardly extending retaining surface formed upon said front vest panel of said universal orthopedic recuperative garment.

12. A universal orthopedic recuperative garment as defined in claim 11 wherein:
   said first transverse rectangular strip mounted on said free end of said arm support panel is composed of a hook type fastening material to releasably connect to said generally rectangular retaining pad; and
   said first and second fastening patches mounted on said arm rotating and binding strap are composed of a hook type fastening material.

13. A universal orthopedic recuperative garment as defined in claim 12 wherein said means connected to adjacent lateral edges of said front and back panels comprises:
   an adjustable strap for adjustably connecting said front and back panels substantially at lateral rib cage areas for securing said vest portion about the upper torso of a patient by shortening or elongating said adjustable strap.

14. A universal orthopedic recuperative garment as defined in claim 13 wherein:
   said adjustable strap encircles the lower torso of a patient when connected at the lateral rib cage areas forming a continuous band around the patient's lower torso being securely fastened to a bottom edge of said front and back panels and adjustable at the lateral rib cage areas.

* * * * *